(12) United States Patent
Iwai et al.

(10) Patent No.: US 8,564,764 B2
(45) Date of Patent: Oct. 22, 2013

(54) BLOOD EXAMINATION APPARATUS

(75) Inventors: Hidenao Iwai, Hamamatsu (JP); Toyohiko Yamauchi, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 647 days.

(21) Appl. No.: 12/676,277

(22) PCT Filed: Jul. 18, 2008

(86) PCT No.: PCT/JP2008/063059
§ 371 (c)(1),
(2), (4) Date: Apr. 1, 2010

(87) PCT Pub. No.: WO2009/031366
PCT Pub. Date: Mar. 12, 2009

(65) Prior Publication Data
US 2010/0220312 A1   Sep. 2, 2010

(30) Foreign Application Priority Data

Sep. 5, 2007   (JP) ............................... P2007-230557

(51) Int. Cl.
| G01N 33/48 | (2006.01) |
| G01N 21/00 | (2006.01) |
| G01N 21/75 | (2006.01) |
| G01N 21/64 | (2006.01) |
| G06K 9/00  | (2006.01) |

(52) U.S. Cl.
USPC ............. 356/39; 382/133; 382/134; 436/164; 422/82.05; 250/461.2

(58) Field of Classification Search
None
See application file for complete search history.

(56) References Cited

U.S. PATENT DOCUMENTS 3,413,464 A    11/1968   Kamentsky
3,947,123 A *   3/1976   Carlson et al. .................. 356/39

(Continued)

FOREIGN PATENT DOCUMENTS

JP    63-144257    6/1988
JP    64-047950    2/1989

(Continued)

OTHER PUBLICATIONS

M. Cristofanilli, M.D. et al., "Circulating Tumor Cells, Disease Progression, and Survival in Metastatic Breast Cancer," The New England Journal of Medicine, Aug. 19, 2004, vol. 351, No. 8, pp. 781-791.

L. W. M. M. Terstappen et al., "Peripheral blood tumor cell load reflects the clinical activity of the disease in patients with carcinoma of the breast," International Journal of Oncology, 2000, vol. 17, pp. 573-578.

(Continued)

*Primary Examiner* — Gordon Stock, Jr.
(74) *Attorney, Agent, or Firm* — Drinker Biddle & Reath LLP

(57) ABSTRACT

This blood examination apparatus examines cancer cells mixed in an examination object which is flowing blood, and includes: a flow cell through which the examination object is made to flow; an imaging optical system which light output from the examination object in an examination region in the flow cell enters, the imaging optical system forming an image of the light on a first image plane; a first Fourier transformation optical system which optically two-dimensionally Fourier-transforms the image formed on the first image plane by the imaging optical system to form the Fourier-transformed image on a second image plane; a spatial light filter which selectively allows a portion in a certain range around an optical axis of the first Fourier transformation optical system of the image formed on the second image plane by the first Fourier transformation optical system to pass through; and a second Fourier transformation optical system which optically two-dimensionally Fourier-transforms the portion which has passed through the spatial light filter of the image formed on the second image plane by the first Fourier transformation optical system to form the Fourier-transformed image on a third image plane.

3 Claims, 7 Drawing Sheets

(56) References Cited

U.S. PATENT DOCUMENTS

| | | | |
|---|---|---|---|
| 4,213,036 A * | 7/1980 | Kopp et al. ............... | 382/133 |
| 5,371,368 A * | 12/1994 | Alfano et al. ............. | 250/341.1 |
| 5,374,989 A | 12/1994 | Takemura et al. | |
| 5,799,656 A * | 9/1998 | Alfano et al. ............. | 600/473 |
| 5,854,710 A * | 12/1998 | Rao et al. .................. | 359/559 |
| 6,337,472 B1 * | 1/2002 | Garner et al. ............. | 250/201.3 |
| 6,665,557 B1 * | 12/2003 | Alfano et al. ............. | 600/473 |
| 7,911,617 B2 * | 3/2011 | Padmanabhan et al. ...... | 356/450 |
| 8,131,053 B2 * | 3/2012 | Ortyn et al. ................ | 382/133 |
| 8,184,298 B2 * | 5/2012 | Popescu et al. ............ | 356/450 |
| 2004/0136577 A1 * | 7/2004 | Rao et al. ................... | 382/128 |
| 2009/0060303 A1 * | 3/2009 | Douglass et al. ........... | 382/128 |
| 2011/0212440 A1 * | 9/2011 | Viovy et al. ................ | 435/6.1 |

FOREIGN PATENT DOCUMENTS

| | | |
|---|---|---|
| JP | 05-045282 | 2/1993 |
| JP | H06-067120 | 3/1994 |
| JP | 06-138417 | 5/1994 |
| JP | 2582797 | 11/1996 |
| JP | H8-287255 | 11/1996 |
| JP | 2001-108684 | 4/2001 |

OTHER PUBLICATIONS

H. Ben Hsieh et al., "High speed detection of circulating tumor cells," Biosensors and Bioelectronics, 2006, vol. 21, pp. 1893-1899.

L. A. Liotta et al., "Quantitative Relationships of Intravascular Tumor Cells, Tumor Vessels, and Pulmonary Metastases following Tumor Implantation," Cancer Rearch, May 1974, vol. 34, pp. 997-1004.

G. Vona et al., "Isolation by Size of Epithelial Tumor Cells," American Journal of Pathology, Jan. 2000, vol. 156, No. 1, pp. 57-63.

P. Rostagno et al., "Detection of Rare Circulating Breast Cancer Cells by Filtration Cytometry and Identification by DNA Content: Sensitivity in an Experimental Model,"Anticancer Research, 1997, vol. 17, pp. 2481-2485.

A. Allan et al., "Detection and Quantification of Circulating Tumor Cells in Mouse Models of Human Breast Cancer Using Immunomagnetic Enrichment and Multiparameter Flow Cytometry," Cytometry Part A, 2005, vol. 65A, pp. 4-14.

H. Gross et al., "Detection of Rare Cells at a Frequency of One Per Million by Flow Cytometry;" Cytometry, 1993, vol. 14, pp. 519-526.

H. Gross et al., "Model study detecting breast cancer cells in peripheral blood mononuclear cells at frequencies as low as $10^{-7}$," Proc. Natl. Acad. Sci. USA, Jan. 1995, vol. 92, pp. 537-541.

J. Leary, "Strategies for Rare Cell Detection and Isolation," Methods in Cell Biology, 1994, vol. 42, pp. 331-358.

* cited by examiner

BLOOD EXAMINATION APPARATUS

TECHNICAL FIELD

The present invention relates to an apparatus for examining blood without staining.

BACKGROUND ART

In recent years, in the medical and biotechnology fields, circulating tumor cells which are cancer cells invading blood from cancer tissue have attracted attention (refer to Non-Patent Document 1). That is, as one of the cancer metastasis mechanisms, there is hematogenous dissemination in which cancer cells developed in a certain organ are transported by blood and metastasize to other organs. It has been expected that metastasis of cancer can be suppressed by removing cancer cells in blood. It is hoped that if living cancer cells can be captured from blood, this will contribute to the development of medicines as antibodies, and the properties and mechanisms of metastasis of cancer will be unraveled.

Blood cells in blood are briefly classified into red blood cells and white blood cells. Approximately $5 \times 10^9$ red blood cells are contained in 1 mL of whole blood. On the other hand, approximately $5 \times 10^6$ to $1 \times 10^7$ white blood cells are contained in 1 mL of whole blood. That is, it is said that the concentration of white blood cells is $1/500$ to $1/1000$ of that of the red blood cells. A red blood cell has a disk shape, a diameter of 7 to 8.8 μm, and a thickness of 2 to 3 μm. White blood cells are classified into monocytes, granulocytes, and lymphocytes. The size of a monocyte is 13 to 21 μm, the size of a granulocyte is 10 to 18 μm, and the size of a lymphocyte is 7 to 16 μm. The abundance ratio of monocytes, granulocytes, and lymphocytes is 7:57:36.

On the other hand, cancer cells which break the basement membrane and mix with blood from cancer tissue have a size of approximately 20 μm, and their nuclei are hypertrophied. The ratio of cancer cells to nucleated cells (white blood cells) in blood is $1/10^7$, and the number of cancer cells per 1 mL of blood is 1 (refer to Non-Patent Documents 2 and 3). Approximately 90% of cancer cells can be discriminated based on only their sizes from blood cells (refer to Non-Patent Document 4).

As a technique for separating cancer cells from blood, a method using a physical mesh by utilizing the size difference between blood cells and cancer cells is known (refer to Non-Patent Documents 5 and 6). However, this physical mesh is easily clogged.

Generally, it is said that the blood volume of a human is 7 to 8% of his/her body weight, and the blood volume of an adult is estimated to be approximately 5000 mL. When the total amount of blood is examined, the examinee is confined during examination, so that the throughput of the blood examination apparatus is a very important factor. The most standard apparatus for examining cells is flow cytometry.

The processing ability of this flow cytometry is 100,000 blood cells per second at most. Focusing on only the number of white blood cells, approximately $10^7$ white blood cells are contained in 1 mL of blood, so that when 5000 mL of blood is examined by flow cytometry, the examination takes 150 hours. In actuality, it has been attempted to detect cancer cells in blood by using flow cytometry (refer to Non-Patent Documents 7 to 9), however, the flow cytometry is not an apparatus intended to examine as much blood as 5000 mL.

In the flow cytometry, cells are made to flow one by one, and fluorescence and scattered light from individual cells are received by a photodetector, and the waveform of an electric signal output from the photodetector which receives light is analyzed to identify the cells. The throughput of the flow cytometry is rate-controlled to the time (dead time) necessary for such analysis of the waveform of the electric signal (refer to Non-Patent Document 10). Thus, according to the flow cytometry, living cells cannot be identified at a frequency of $1/10^7$ (1 per 1 mL of blood) from 5000 mL of blood.

It is possible that blood is imaged by using a CCD camera or a CMOS camera and the image obtained through the imaging is analyzed to examine whether a cancer cell is present in the image. CCD cameras and CMOS cameras have been increased in speed according to improvement in imaging techniques, however, the frame rate is 5 kHz at most, and the image update time interval is 200 μsec. On the other hand, the migration speed of cells in the flow cytometry is several meters per second. For example, in a microscopic objective lens field of 40 times (approximately 0.5 mm square), a cell moving at a speed of 1 m/sec passes through the field (comes out of the frame) in 500 μsec. Therefore, it is not realistic to find cancer cells in a large amount of blood by analyzing images taken by a CCD camera or a CMOS camera.

A technique for identifying cancer cells in blood by using a matched filter (holographic filter) method (refer to Patent Document 1) is known. According to this technique, a pattern of diffracted light generated from blood irradiated with a laser beam is formed, and an image of light output from a matched filter disposed on the diffracted light pattern formed surface is imaged by a CCD camera, and by analyzing the image obtained through this imaging, the position, etc., of a cancer cell in blood is detected. However, this technique also requires analysis of the images taken by the CCD camera, and therefore, it is not realistic to find cancer cells in a large amount of blood. In Patent Document 1, a detailed matched filter shape for finding cancer cells in blood is not described, and the problem is unsolved.

Patent Document 1: Japanese Patent Registration No. 2582797
Non-Patent Document 1: M. Cristofanilli, et al., The New England Journal of Medicine, Vol. 351, pp. 781-791, (2004).
Non-Patent Document 2: L. W. M. M. Terstappen, et al., International Journal of Oncology, Vol. 17, pp. 573-578, (2000).
Non-Patent Document 3: H. B. Hsieh, et al., Biosensors and Bioelectronics, Vol. 21, pp. 1893-1899, (2006).
Non-Patent Document 4: L. A. Liotta, et al., Cancer Research, Vol. 34, pp. 997-1004, (1974).
Non-Patent Document 5: G. Vona, et al., American Journal of Pathology, Vol. 156, No. 1, pp. 57-63, (2000).
Non-Patent Document 6: P. Rostagno, et al., Anticancer Research, Vol. 17, pp. 2481-2485, (1997).
Non-Patent Document 7: A. L. Allan, et al., Cytometry Part A, Vol. 65A, pp. 4-14, (2005).
Non-Patent Document 8: H-J. Gross, et al., Cytometry, Vol. 14, pp. 519-526, (1993).
Non-Patent Document 9: H-J. Gross, et al., Proc. Natl. Acad. Sci. USA, Vol. 92, pp. 537-541, (1995).
Non-Patent Document 10: J. F. Leary, Methods in Cell Biology, Vol. 42, Chapter 20, pp. 331-358, (1994).

DISCLOSURE OF THE INVENTION

Problems to be Solved by the Invention

As described above, identification and position identification of cancer cells in blood cannot be performed at a high speed by any of the techniques using a physical mesh as described in Non-Patent Documents 5 and 6, flow cytometry as described in Non-Patent Documents 7 to 10, and the technique using a matched filter as described in Patent Document 1.

The present invention was made for solving the above-described problem, and an object thereof is to provide a blood examination apparatus which can perform identification and position identification of cancer cells in blood at a high speed without staining.

Means for Solving the Problems

A blood examination apparatus according to the present invention for examining cancer cells mixed in an examination object which is flowing blood includes: (1) a flow cell through which the examination object is made to flow; (2) an imaging optical system which light output from the examination object in an examination region in the flow cell enters, the imaging optical system forming an image of the light on a first image plane; (3) a first Fourier transformation optical system which optically two-dimensionally Fourier-transforms the image formed on the first image plane by the imaging optical system to form the Fourier-transformed image on a second image plane; (4) a spatial light filter which selectively allows a portion in a certain range around an optical axis of the first Fourier transformation optical system of the image formed on the second image plane by the first Fourier transformation optical system to pass through; and (5) a second Fourier transformation optical system which optically two-dimensionally Fourier-transforms the portion which has passed through the spatial light filter of the image formed on the second image plane by the first Fourier transformation optical system to form the Fourier-transformed image on a third image plane.

In the blood examination apparatus according to the present invention, an image of light output from the examination object in the examination region in the flow cell is formed on the first image plane by the imaging optical system. The image formed on the first image plane by the imaging optical system is optically two-dimensionally Fourier-transformed by the first Fourier transformation optical system, and the Fourier-transformed image is formed on the second image plane. A portion in a certain range around the optical axis of the first Fourier transformation optical system of the image formed on the second image plane by the first Fourier transformation optical system is selectively allowed to pass through the spatial light filter. Then, the portion which has passed through the spatial light filter of the image formed on the second image plane by the first Fourier transformation optical system is optically two-dimensionally Fourier-transformed by the second Fourier transformation optical system, and the Fourier-transformed image is formed on the third image plane.

In this case, the image formed on the third image plane by the second Fourier transformation optical system does not contain a component with a high spatial frequency in the image formed on the first image plane while it contains a component with a small spatial frequency. Further, in the image formed on the first image plane, a region of a cancer cell image portion is wider than a blood cell image portion. Accordingly, in the image formed on the third image plane, the cancer cell image portion appears more clearly than the blood cell image portion. Therefore, based on the image formed on the third image plane, information on the presence or position of a cancer cell in the examination object can be obtained.

The above-described blood examination apparatus preferably further includes: (6) a photodetection section which detects a light amount of the image formed on the third image plane by the second Fourier transformation optical system; (7) a flow channel switch section which is provided on the downstream of the examination region of the flow cell, and makes the examination object flowing through the flow cell selectively flow to either a first branched flow channel or a second branched flow channel; and (8) a controller which controls the flow channel switch section to make the examination object flow to the first branched flow channel when the light amount detected by the photodetection section is larger than a threshold, and controls the flow channel switch section to make the examination object flow to the second branched flow channel when the light amount detected by the photodetection section is not more than the threshold. In this case, the light amount of the image formed on the third image plane by the second Fourier transformation optical system is detected by the photodetection section. Then, the flow channel switch section provided on the downstream of the examination region of the flow cell is controlled by the controller so that the examination object flowing through the flow cell flows to the first branched flow channel when the light amount detected by the photodetection section is larger than the threshold, and flows to the second branched flow channel when the light amount detected by the photodetection section is not more than the threshold.

The above-described blood examination apparatus preferably further includes a laser beam irradiation section which convergently irradiates a laser beam onto a position within the examination region corresponding to a bright spot position in the image formed on the third image plane by the second Fourier transformation optical system. In this case, a laser beam is convergently irradiated by the laser beam irradiation section onto a position inside the examination region corresponding to a bright spot position in the image formed on the third image plane by the second Fourier transformation optical system. At this convergent irradiation position, a cancer cell is present, so that the cancer cell can also be discriminated according to the theory of optical tweezers. By increasing the laser beam power, the cancer cell can be killed.

In the blood examination apparatus described above, the spatial light filter preferably selectively allows a ring region with a certain distance from the optical axis in a light beam section to pass through. In this case, this spatial light filter serves as a bandpass filter.

Effect of the Invention

According to the present invention, identification and position identification of cancer cells in blood can be performed at a high speed.

Figure 1:
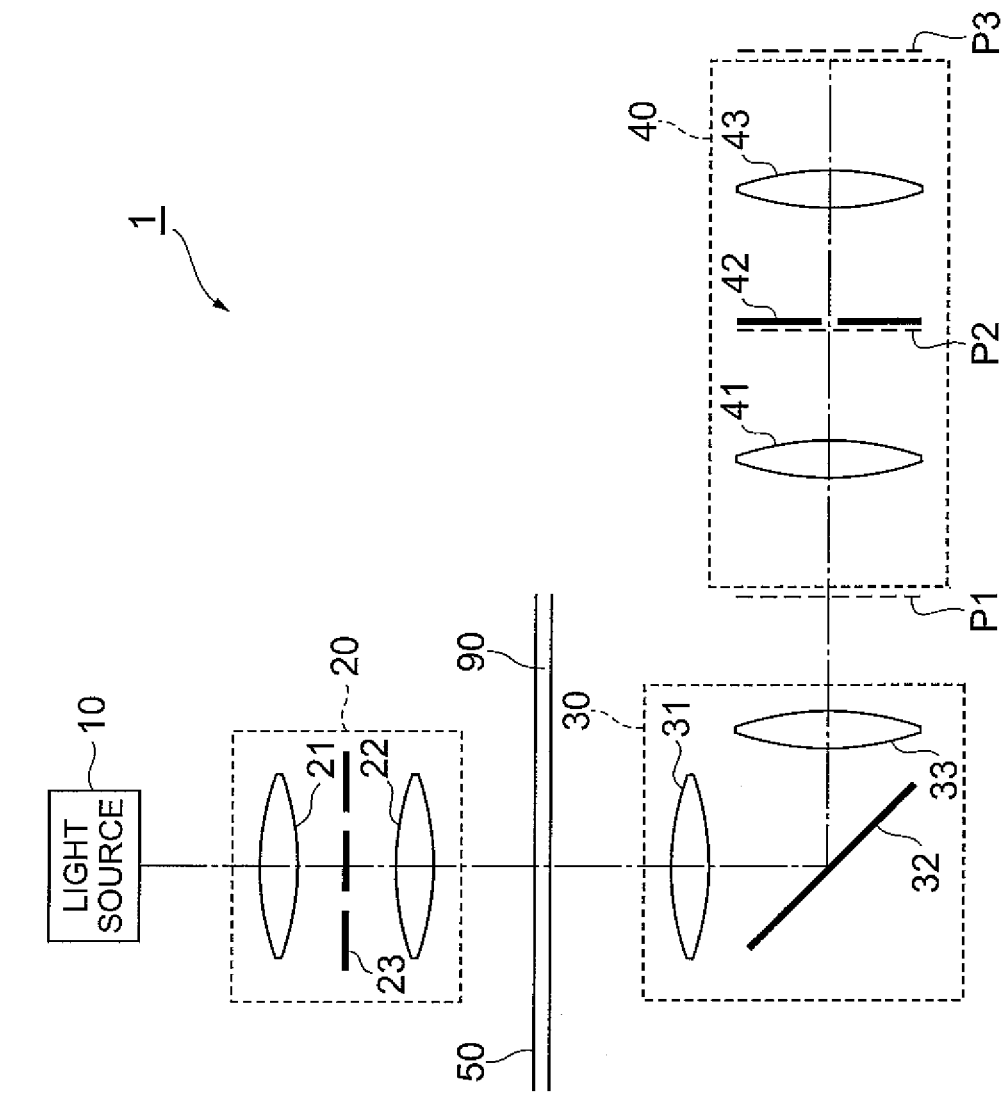
FIG. 1 is a configuration view of a blood examination apparatus 1 according to the present embodiment.

DESCRIPTION OF SYMBOLS 1 to 3: Blood examination apparatus, 10: Light source, 20: Irradiation optical system, 21: Collector lens, 22: Condenser lens, 23: Diaphragm plate, 30: Imaging optical system, 31: Objective lens, 32: Mirror, 33: Imaging lens, 40: Detection optical system, 41: First Fourier transformation optical system, 42: Spatial light filter, 43: Second Fourier transformation optical system, 50: Flow cell, 51: First branched flow channel, 52: Second branched flow channel, 60: Photodetection section, 61: Lens, 62: Neutral density filter, 63: Detector, 70: Flow channel switch section, 71: Controller, 80: Laser beam irradiation section, 81: Mirror, 82: Lens, 83: Mirror, 84: Photodiode array, 85: VCSEL device array, 86: Lens, 87: Lens, 88: Half mirror, 90: Examination object, 91: Blood cell, 92: Cancer cell, P1: First image plane, P2: Second image plane, P3: Third image plane.

BEST MODES FOR CARRYING OUT THE INVENTION

Hereinafter, best modes for carrying out the present invention will be described in detail with reference to the accompanying drawings. In the description of the drawings, the same components are designated by the same reference numerals and letters, and overlapping description will be omitted.

FIG. 1 is a configuration view of a blood examination apparatus 1 according to the present embodiment. The blood examination apparatus 1 shown in this figure includes a light source 10, an irradiation optical system 20, an imaging optical system 30, a detection optical system 40, and a flow cell 50. Among these, the light source 10, the irradiation optical system 20, and the imaging optical system 30 have the same configurations as those of a phase-contrast microscope. The detection optical system 40 includes a first Fourier transformation optical system 41, a spatial light filter 42, and a second Fourier transformation optical system 43. The flow cell 50 may be a blood vessel or a lymph vessel, or may be a microscopic slide on which cells are applied. An objective lens 31 included in the imaging optical system 30 is not a simple lens, but may be an objective lens including a phase plate. This phase plate is disposed at a back focal plane of the objective lens 31. When the phase-contrast microscope is used, a special objective lens including such a phase plate is used.

The light source 10 outputs light to be irradiated onto an examination object 90 flowing inside the flow cell 50. The irradiation optical system 20 irradiates the light output from the light source 10 onto a predetermined range of the examination object 90. The irradiation optical system 20 includes a collector lens 21, a diaphragm plate 23, and a condenser lens 22. The collector lens 21 collimates the light emitted and output from the light source 10. The diaphragm plate 23 selectively allows a ring region with a certain distance from the optical axis in the light beam section to pass through to limit the direction of irradiation onto the examination region. The condenser lens 22 converges the light collimated by the collector lens 21 and irradiates it onto the predetermined range of the examination object 90.

Light output from the examination region of the examination object 90 flowing inside the flow cell 50 (light transmitted through the examination object 90 of the light irradiated by the irradiation optical system 20) enters the imaging optical system 30 and the imaging optical system 30 forms a real image of the light on a first image plane P1. The imaging optical system 30 includes an objective lens 31, a mirror 32, and an imaging lens 33. The mirror 32 is inserted in a light path between the objective lens 31 and the imaging lens 33. Light output from the examination region of the examination object 90 enters the objective lens 31 and the objective lens 31 outputs the light to the mirror 32. The mirror 32 reflects light output from the objective lens 31 to the imaging lens 33. Light reflected from the mirror 32 enters the imaging lens 33 and the imaging lens 33 forms a real image of the light on the first image plane P1. At this time, the real image formed on the first image plane P1 is preferably magnified to be larger than the actual examination object 90.

The front focal plane of the first Fourier transformation optical system 41 matches with the first image plane P1, and the back focal plane of the first Fourier transformation optical system 41 matches with the second image plane P2. The first Fourier transformation optical system 41 optically two-dimensionally Fourier-transforms the image formed on the first image plane P1 by the imaging optical system 30, and the Fourier-transformed image is formed on the second image plane P2.

Figure 2:
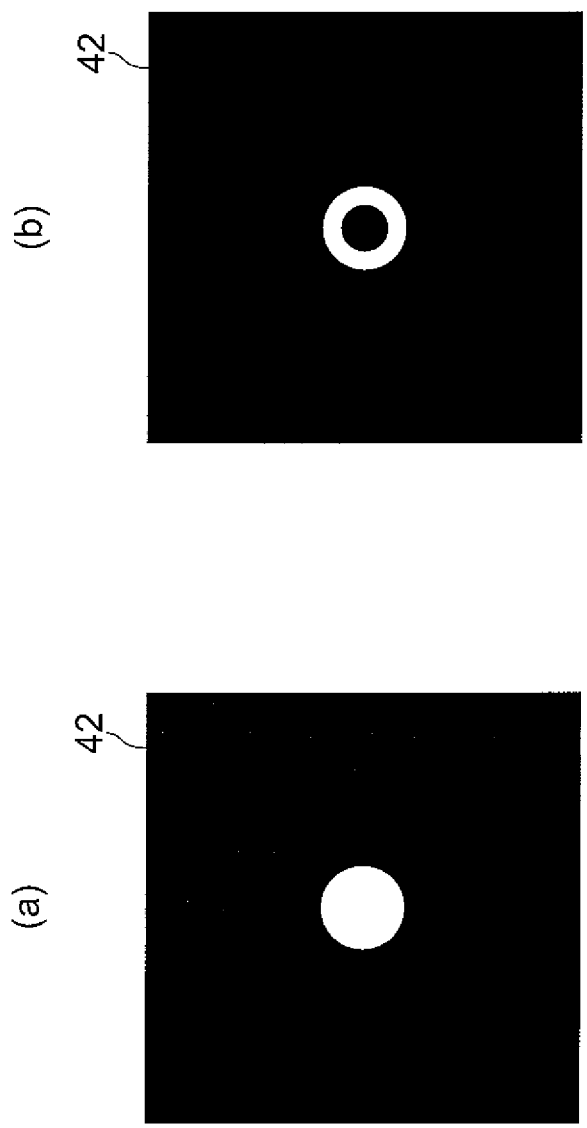
FIG. 2 are views showing a spatial light filter 42 included in the blood examination apparatus 1 according to the present embodiment.

The spatial light filter 42 is provided on the second image plane P2, and selectively allows a portion in a certain range around the optical axis of the first Fourier transformation optical system 41 of the image formed on the second image plane P2 by the first Fourier transformation optical system 41 to pass through. The shape of this passing-through region may be a circular opening (FIG. 2(a)) around the optical axis of the first Fourier transformation optical system 41, or a ring opening (FIG. 2(b)). FIG. 2(a) and FIG. 2(b) are views showing the spatial light filter 42, and the black region shows a light shielding portion, and the white region shows a light passing-through portion.

The spatial light filter 42 which is a circular opening selectively allows a circular region with a distance not more than a predetermined value from the optical axis in the light beam section to pass through, and serves as a low-pass filter. On the other hand, the spatial light filter 42 which is a ring opening selectively allows a ring region with a certain distance from the optical axis in the light beam section to pass through, and serves as a bandpass filter. The size of this passing-through region is 9.2 mm when it is a circular opening, and has roughly an outer diameter of 9.2 mm and an inner diameter of 4.6 mm when it is a ring opening, for example, when the imaging magnification is 1, the size of the image on the first image plane P1 is approximately 300×300 μm, the central wavelength is 0.580 μm, and the focal length of the first Fourier transformation optical system 41 is 400 mm.

For example, the spatial light filter 42 has an aperture in a certain range of an opaque flat plate, and selectively allows light input in the aperture to pass through. Alternatively, for example, the spatial light filter 42 has an opaque film formed in a region other than a window portion in a certain range of a transparent glass plate, and selectively allows light input in the window portion to pass through.

The front focal plane of the second Fourier transformation optical system 43 matches with the second image plane P2, and the back focal plane of the second Fourier transformation optical system 43 matches with the third image plane P3. The second Fourier transformation optical system 43 optically two-dimensionally Fourier-transforms a portion which has passed through the spatial light filter 42 of the image formed on the second image plane P2 by the first Fourier transformation optical system 41 to form the Fourier-transformed image on the third image plane P3.

The examination object 90 flowing in the flow cell 50 is blood. The blood as the examination object 90 may contain not only blood cells but also cancer cells. The flow direction of the examination object 90 in the flow cell 50 is perpendicular to the optical axis direction of the objective lens 31. The blood examination apparatus 1 of the present embodiment examines cancer cells mixed in the blood as the examination object 90. It is preferable that blood flows so that a plurality of cells do not overlap each other in the optical axis direction of the objective lens 31.

The blood examination method using this blood examination apparatus 1 is as follows. Light output from the light source 10 is irradiated onto a predetermined range of the examination object 90 through the irradiation optical system 20 including the collector lens 21, the diaphragm plate 23, and the condenser lens 22. Light output from the examination object 90 (light transmitted through the examination object 90 of the light irradiated by the irradiation optical system 20) passes through the imaging optical system 30 including the objective lens 31, the mirror 32, and the imaging lens 33, and is made incident on the first image plane P1, and a real image is accordingly formed.

The image formed on the first image plane P1 by the imaging optical system 30 is optically two-dimensionally Fourier-transformed by the first Fourier transformation optical system 41, and the Fourier-transformed image is formed on the second image plane P2. A portion in a certain range around the optical axis of the first Fourier transformation optical system 41 of the image formed on the second image plane P2 by the first Fourier transformation optical system 41 is selectively allowed to pass through the spatial light filter 42 and optically two-dimensionally Fourier-transformed by the second Fourier transformation optical system 43, and the Fourier-transformed image is formed on the third image plane P3.

The image to be formed on the second image plane P2 is obtained by optically two-dimensionally Fourier-transforming the image formed on the first image surface P1, and indicates the two-dimensional spatial frequency distribution of the image formed on the first image plane P1. In addition, when assuming the case where the spatial light filter 42 is removed, the image to be formed on the third image plane P3 is obtained by optically two-dimensionally Fourier-transforming the image formed on the second image plane P2, and is equivalent to the image formed on the first image plane P1.

In the image indicating the two-dimensional spatial frequency distribution on the second image plane P2, the position at which the optical axis of the first Fourier transformation optical system 41 crosses the second image plane P2 is defined as an origin, and the spatial frequency becomes smaller as it becomes closer to this origin. In other words, in the image formed on the second image plane P2 by the first Fourier transformation optical system 41, a portion in a certain range around the optical axis of the first Fourier transformation optical system 41 (portion to be selectively allowed to pass through the spatial light filter 42) is a component with a spatial frequency smaller than a certain value. The image formed on the third image plane P3 by the second Fourier transformation optical system 43 contains a component with a small spatial frequency in the image formed on the first image plane P1, but does not contain a component with a high spatial frequency.

Figure 3:
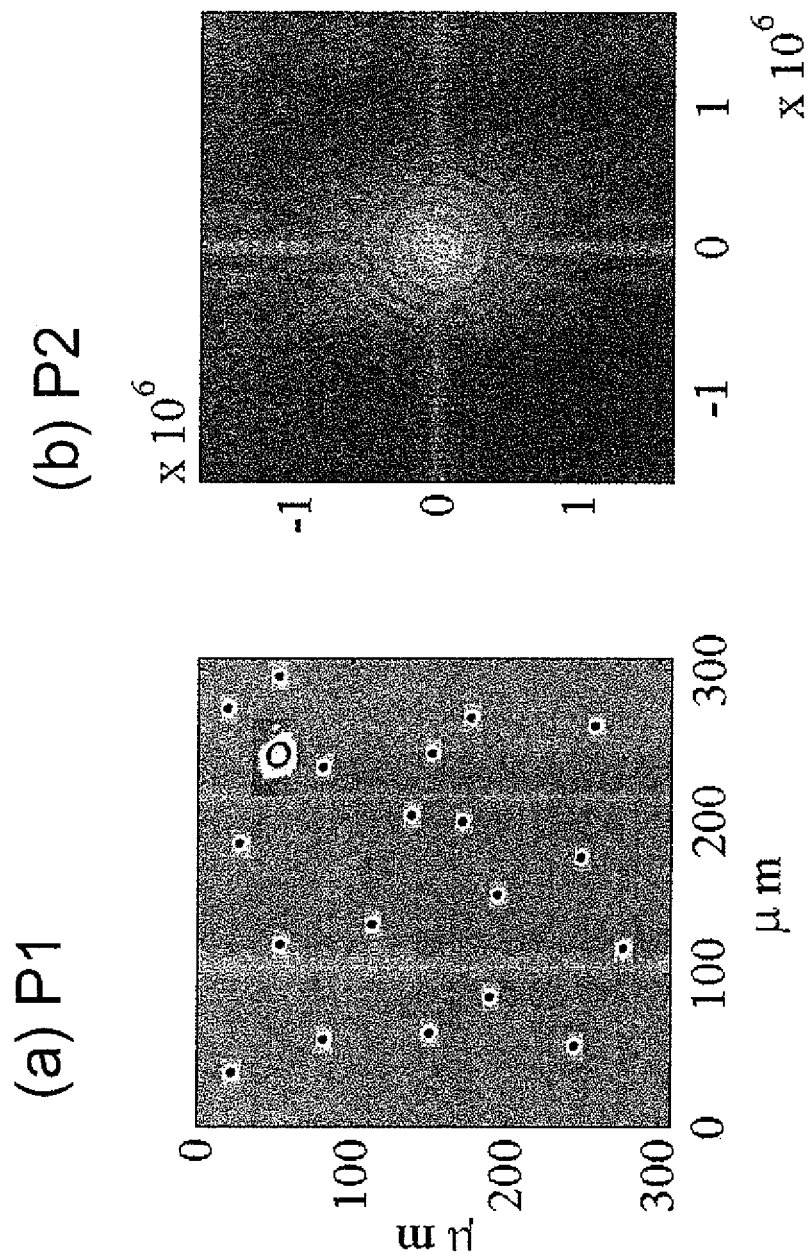
FIG. 3 are views showing examples of images formed on a first image plane P1 and a second image plane P2, respectively, in the present embodiment.
Figure 4:
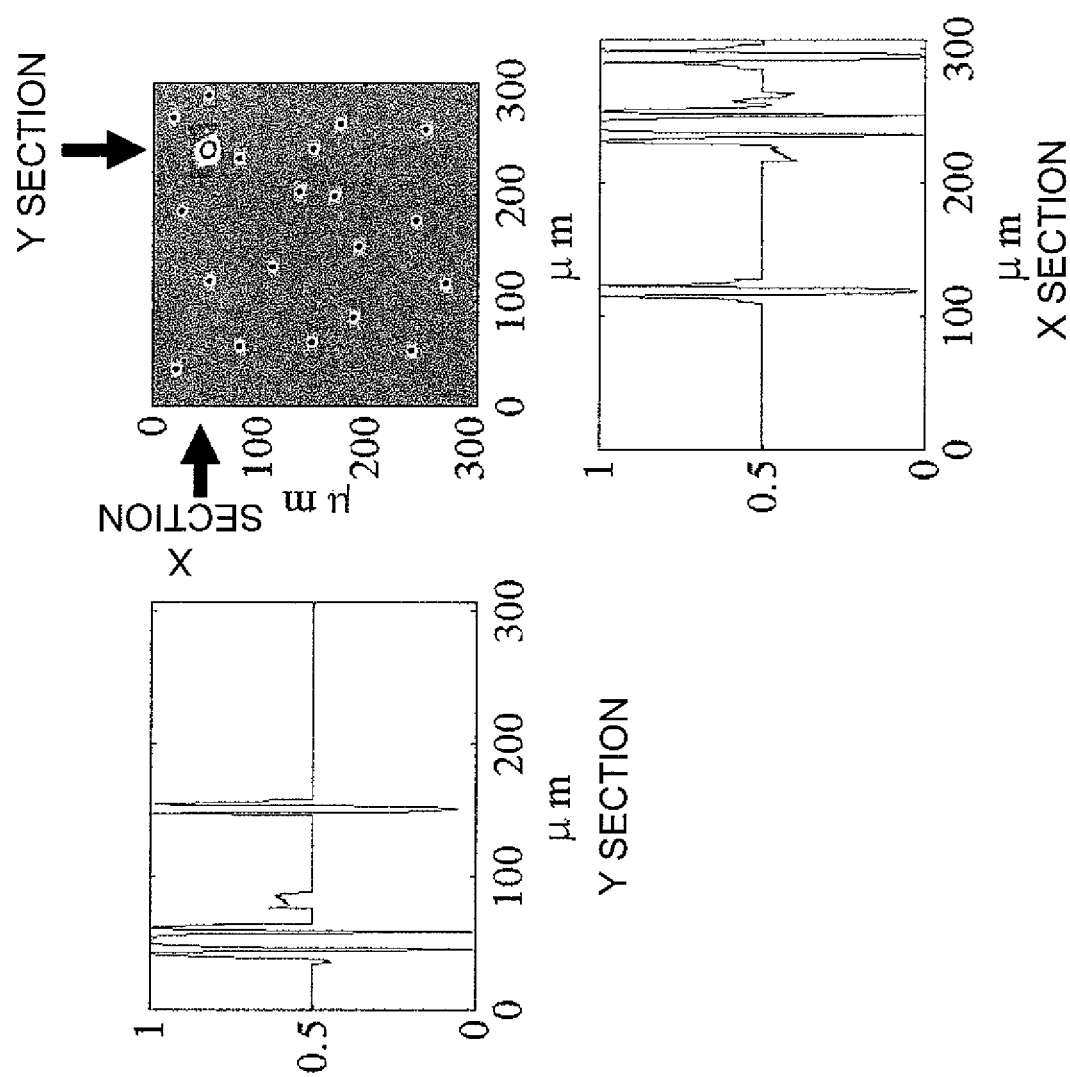
FIG. 4 is a view showing an example of an image formed on the first image plane P1 in the present embodiment.
Figure 5:
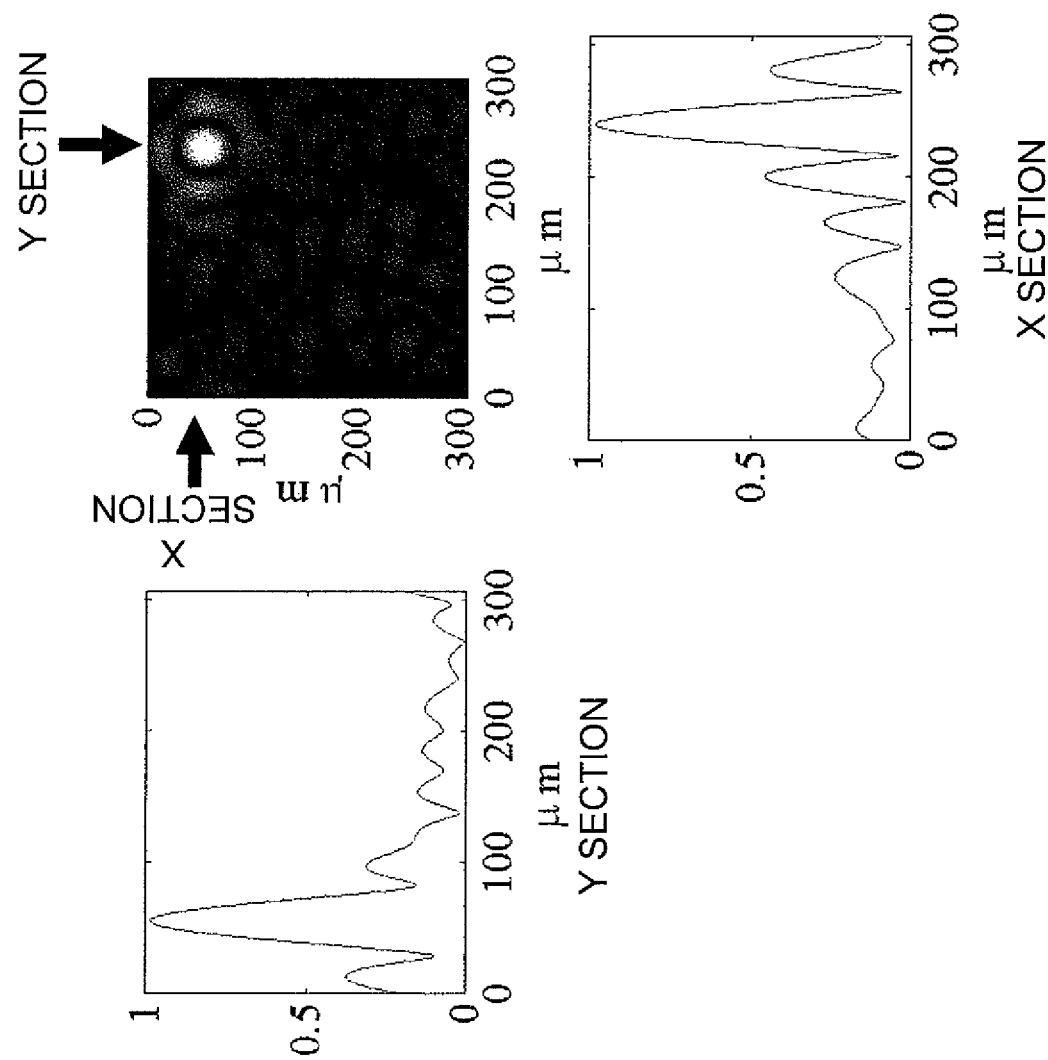
FIG. 5 is a view showing an example of an image formed on a third image plane P3 in the present embodiment.

FIG. 3 are views showing examples of images formed on the first image plane P1 and the second image plane P2, respectively, in the present embodiment. FIG. 3(a) shows an image to be formed on the first image plane P1, and FIG. 3(b) shows an image to be formed on the second image plane P2. FIG. 4 is a view showing an example of an image formed on the first image plane P1 in the present embodiment. FIG. 5 is a view showing an example of an image formed on the third image plane P3 in the present embodiment. Here, the spatial light filter 42 is a ring opening. As shown in FIG. 3(a) and FIG. 4, in the image formed on the first image plane P1, a cancer cell represented as a large black circle is present as well as blood cells represented as small black circles. However, as shown in FIG. 5, in the image formed on the third image plane P3, a distinct bright region is not present at positions at which blood cells are originally present on the first image plane P1, however, at the position at which a cancer cell is originally present on the first image plane P1, a distinct bright region is present.

Thus, from the image on the third image plane P3 as shown in FIG. 5, information on the presence and the position of a cancer cell in the examination object 90 can be directly obtained without image analysis. Therefore, identification and position identification of cancer cells in blood can be performed at a high speed, and this is preferable for examination of a large amount of blood.

Figure 6:
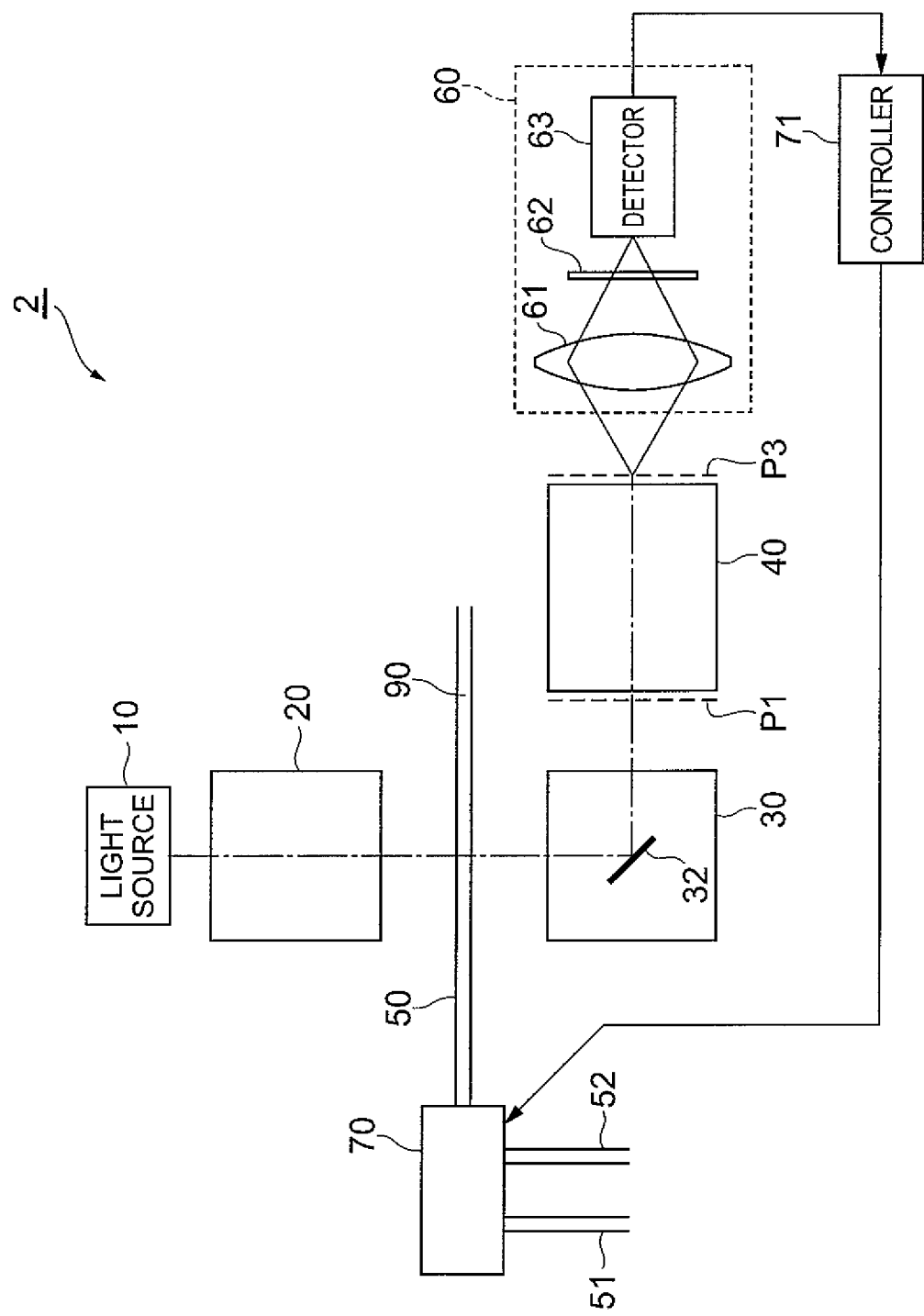
FIG. 6 is a configuration view of a blood examination apparatus 2 according to another embodiment.

FIG. 6 is a configuration view of a blood examination apparatus 2 according to another embodiment. The blood examination apparatus 2 shown in FIG. 6 further includes, in addition to the configuration of the blood examination apparatus 1 shown in FIG. 1, a first branched flow channel 51, a second branched flow channel 52, a photodetection section 60, a flow channel switch section 70, and a controller 71.

The photodetection section 60 detects a light amount of the image formed on the third image plane P3 by the second Fourier transformation optical system 43, and includes a lens 61, a neutral density filter 62, and a detector 63. The photodetection section 60 condenses the image on the third image plane P3 onto a light receiving surface of the detector 63 by the lens 61 and detects the light amount by the detector 63. As the detector 63, for example, a photodiode or a photomultiplier tube is used.

The neutral density filter 62 inserted between the lens 61 and the detector 63 reduces the power of the light to be made incident on the detector 63 to a degree of making the operation of the detector 63 fall within a single-photon region. When the detector 63 operates in a single-photon region, by counting the number of photons reaching the light receiving surface of the detector 63, cancer cells in the examination region can be counted. When examination as to whether a cancer cell is present in the image formed on the third image plane P3 is only required, the neutral density filter 62 is unnecessary, and the presence of a cancer cell can be determined based on comparison between the output value from the detector 63 and a threshold.

The flow channel switch section 70 is provided on the downstream of the examination region of the flow cell 50, and makes the examination object 90 flowing through the flow cell 50 selectively flow to either the first branched flow channel or the second branched flow channel 52. The controller 71 controls the flow channel switch section 70 to make the examination object flow to the first branched flow channel 51 when the light amount detected by the photodetection section 60 is larger than the threshold (that is, the presence of a cancer cell is found). The controller 71 controls the flow channel switch section 70 to make the examination object flow to the second branched flow channel 52 when the light amount detected by the photodetection section 60 is not more than the threshold (that is, the presence of a cancer cell is not found).

Therefore, the examination object 90 flowing to the first branched flow channel 51 contains cancer cells, and the examination object 90 flowing to the second branched flow channel 52 does not contain a cancer cell. The examination object 90 flowing to the first branched flow channel 51 contains not only cancer cells but also blood cells, however, the cancer cells are concentrated, so that this can contribute to development of medicines as antibodies and the properties and mechanisms of metastasis of cancer will be unraveled.

Figure 7:
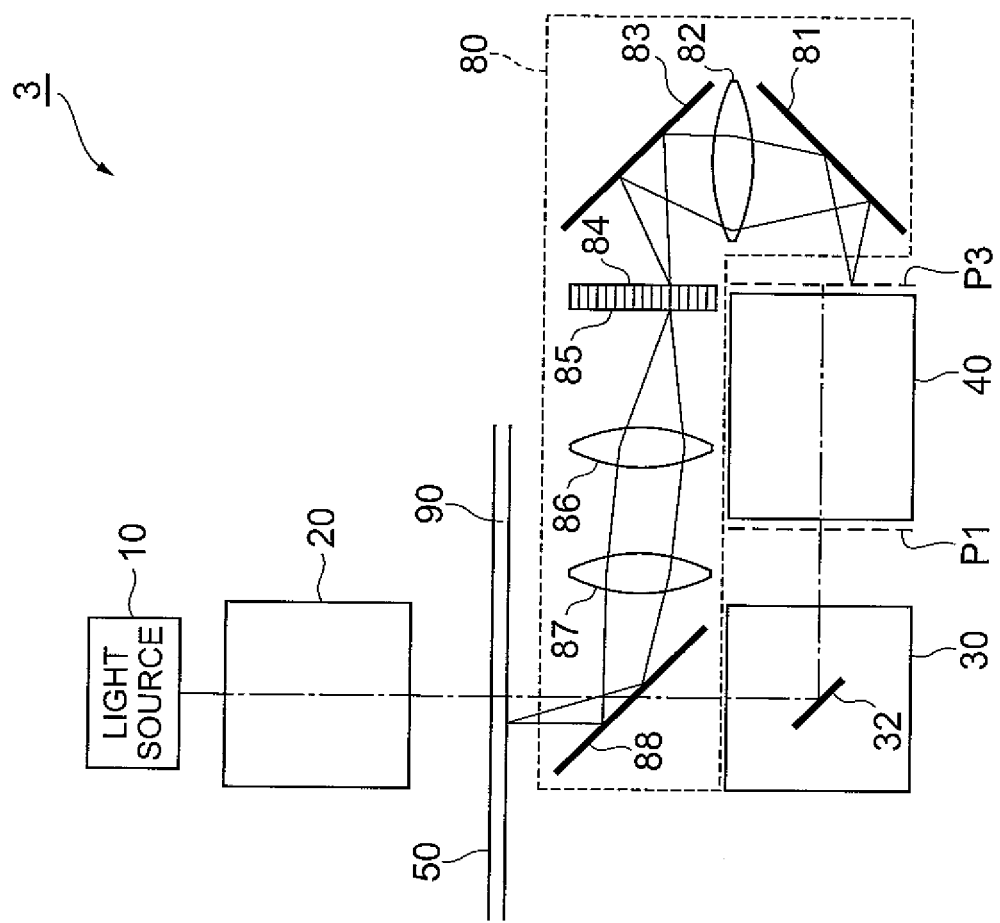
FIG. 7 is a configuration view of a blood examination apparatus 3 according to still another embodiment.

FIG. 7 is a configuration view of a blood examination apparatus 3 according to still another embodiment. The blood examination apparatus 3 shown in FIG. 7 further includes, in addition to the configuration of the blood examination apparatus 1 shown in FIG. 1, a laser beam irradiation section 80. The laser beam irradiation section 80 convergently irradiates a laser beam onto a position in an examination region corresponding to a bright spot position in the image formed on the third image plane P3 by the second Fourier transformation optical system 43, and includes a mirror 81, a lens 82, a mirror 83, a photodiode array 84, a VCSEL (vertical cavity surface emitting laser) device array 85, a lens 86, a lens 87, and a half mirror 88.

The lens 82 re-images the image formed on the third image plane P3 by the second Fourier transformation optical system 43 on the photodiode array 84. The mirror 81 is provided on the light path between the third image plane P3 and the lens 82. The mirror 83 is provided on the light path between the lens 82 and the photodiode array 84. These mirrors 81 and 83 are provided for turning-back the light path.

The photodiode array 84 is formed by two-dimensionally arraying a plurality of photodiodes on a plane. The VCSEL device array 85 is formed by two-dimensionally arraying a plurality of VCSEL devices on a plane. The individual photodiodes included in the photodiode array 84 and the individual VCSEL devices included in the VCSEL device array 85 correspond to each other at a ratio of 1 to 1. When light is made incident on any of the photodiodes included in the photodiode array 84, the VCSEL device corresponding to this photodiode outputs a laser beam.

The photodiode array 84 may be replaced by a PSD (Position Sensitive Device). Position information X and Y outputs from the PSD are input into the capable of addressing VCSEL device array 85. A probability of simultaneous appearance of a plurality of cancer cells in the examination region is very low based on the fact that the cancer cell frequency in blood is $1/10^7$ of the nucleated cells (white blood cells), so that a photodetector such as the PSD can also be used.

When any of the VCSEL devices included in the VCSEL device array 85 outputs a laser beam, lenses 86 and 87 and the half mirror 88 convergently irradiate the laser beam onto the examination region of the examination object 90 in the flow cell 50. The convergent irradiation position corresponds to the position of the VCSEL device which has emitted the laser beam in the VCSEL device array 85, corresponds to the position of the photodiode which has received the laser beam in the photodiode array 84, and corresponds to the position of the bright spot on the third image plane P3. Therefore, at the laser beam convergent irradiation position, a cancer cell is present. Thus, by convergently irradiating a laser beam onto a cancer cell in the examination object 90, according to the theory of optical tweezers and a light pressure, the cancer cell can be discriminated. By increasing the laser beam power, the cancer cell can be killed.

The present invention is not limited to the above-described embodiments, and can be variously changed. For example, the blood examination apparatus 1 according to the embodiment described above includes the configuration of a phase-contrast microscope, however, the blood examination apparatus according to the present invention may include a microscope of another type, such as a transmissive bright field microscope, a reflective bright field microscope, a dark field microscope, a differential interference microscope, or a quantitative phase microscope. On the other hand, when a phase-contrast microscope and a differential interference microscope are used respectively, even if a cell is colorless and transparent, the cell can be detected without staining the cell. The quantitative phase microscope quantitatively obtains a phase difference of a specimen, and not only adds contrast to a colorless and transparent cell, but also converts optical thickness into luminance information. This aids in enhancing the contrast in FIG. 3(*a*) in identification of a cancer cell from blood cells.

In the phase-contrast microscope, a phase plate for adjusting the phase difference between direct light (S wave) passing through a cell and diffracted light (D wave) passing through a surrounding medium is disposed on the back focal plane of the objective lens, and by making the S wave and the D wave interfere with each other on the first image plane P1, the phase difference between the cell and the medium can be converted into a tone difference on the first image plane P1. Depending on the phase difference adjustment amount on the phase plate, the cell with a refractive index higher than that of the medium becomes a dark region (positive contrast) on the first image plane P1, or a cell with a refractive index higher than that of the medium becomes a bright region (negative contrast) on the first image plane P1.

The invention claimed is:

1. A blood examination apparatus for examining cancer cells mixed in an examination object which is flowing blood, comprising:
   a flow cell through which the examination object is made to flow;
   an imaging optical system which light output from the examination object in an examination region in the flow cell enters, the imaging optical system forming an image of the light on a first image plane;
   a first Fourier transformation optical system which optically two-dimensionally Fourier-transforms the image formed on the first image plane by the imaging optical system to form the Fourier-transformed image on a second image plane;
   a spatial light filter which selectively allows a portion in a certain range around an optical axis of the first Fourier transformation optical system of the image formed on the second image plane by the first Fourier transformation optical system to pass through; and
   a second Fourier transformation optical system which optically two-dimensionally Fourier-transforms the portion which has passed through the spatial light filter of the image formed on the second image plane by the first Fourier transformation optical system to form the Fourier-transformed image on a third image plane;
   a photodetection section which detects a light amount of the image formed on the third image plane by the second Fourier transformation optical system;
   a flow channel switch section which is provided on the downstream of the examination region of the flow cell, and makes the examination object flowing through the flow cell selectively flow to either a first branched flow channel or a second branched flow channel; and
   a controller which controls the flow channel switch section to make the examination object flow to the first branched flow channel when the light amount detected by the photodetection section is larger than a threshold, and controls the flow channel switch section to make the examination object flow to the second branched flow channel when the light amount detected by the photodetection section is not more than the threshold.

2. The blood examination apparatus according to claim 1, further comprising: a laser beam irradiation section which convergently irradiates a laser beam onto a position within the examination region corresponding to a bright spot position in the image formed on the third image plane by the second Fourier transformation optical system.

3. The blood examination apparatus according to claim 1, wherein the spatial light filter selectively allows a ring region with a certain distance from the optical axis in a light beam section to pass through.

* * * * *

UNITED STATES PATENT AND TRADEMARK OFFICE
CERTIFICATE OF CORRECTION

PATENT NO.         : 8,564,764 B2
APPLICATION NO.    : 12/676277
DATED              : October 22, 2013
INVENTOR(S)        : Iwai et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 674 days.

Signed and Sealed this
Fifteenth Day of September, 2015

Michelle K. Lee
*Director of the United States Patent and Trademark Office*